(12) United States Patent
Lurie

(10) Patent No.: US 7,185,649 B2
(45) Date of Patent: Mar. 6, 2007

(54) SYSTEMS AND METHODS FOR INCREASING CEREBRAL SPINAL FLUID FLOW

(75) Inventor: Keith G. Lurie, Minneapolis, MN (US)

(73) Assignee: Advanced Circulatory Systems Inc., Eden Prairie, MN (US)

( * ) Notice: Subject to any disclaimer, the term of this patent is extended or adjusted under 35 U.S.C. 154(b) by 513 days.

(21) Appl. No.: 10/460,558

(22) Filed: Jun. 11, 2003

(65) Prior Publication Data

US 2004/0211416 A1    Oct. 28, 2004

Related U.S. Application Data

(63) Continuation-in-part of application No. 10/426,161, filed on Apr. 28, 2003.

(51) Int. Cl.
*A61M 16/00* (2006.01)
*A62B 9/02* (2006.01)
*A62B 7/10* (2006.01)
*A62B 18/10* (2006.01)

(52) U.S. Cl. .......................... 128/203.11; 128/202.28; 128/205.24; 128/206.15; 128/207.12

(58) Field of Classification Search .......... 128/202.28, 128/202.29, 203.11, 205.24, 205.25, 206.12, 128/206.15, 206.18, 206.21, 206.28, 207.12, 128/207.13, 207.16; 137/102, 846
See application file for complete search history.

(56) References Cited

U.S. PATENT DOCUMENTS

| | | | |
|---|---|---|---|
| 2,774,346 A | 12/1956 | Halliburton | |
| 3,077,884 A | 2/1963 | Batrow et al. | |
| 3,191,596 A * | 6/1965 | Bird et al. | 128/204.19 |
| 3,307,541 A | 3/1967 | Hewson | |
| 3,459,216 A | 8/1969 | Bloom et al. | |
| 3,515,163 A | 6/1970 | Freeman | |
| 3,662,751 A * | 5/1972 | Barkalow et al. | 128/204.25 |
| 3,669,108 A * | 6/1972 | Sundblom et al. | 128/204.26 |

(Continued)

FOREIGN PATENT DOCUMENTS

CA              668771              8/1963

(Continued)

OTHER PUBLICATIONS

Christenson, J.M., "Abdominal Compressions During CPR: Hemodynamic Effects of Altering Timing and Force", The Journal of Emergency Medicine, vol. 10, pp. 257-266, 1992.

(Continued)

*Primary Examiner*—Henry Bennett
*Assistant Examiner*—Annette Dixon
(74) *Attorney, Agent, or Firm*—Townsend and Townsend and Crew LLP

(57) ABSTRACT

In one embodiment, the invention provides a device for decreasing intracranial or intraocular pressures. The device comprises a housing having an inlet opening and an outlet opening that is adapted to be interfaced with a person's airway. The device further includes a valve system that is operable to regulate respiratory gas flows through the housing and into the person's lungs during spontaneous or artificial inspiration. The valve system assists in lowering intrathoracic pressures during each inspiration to repetitively lower pressures in the venous blood vessels that transport blood out of the head to thereby reduce intracranial or intraocular pressures.

12 Claims, 9 Drawing Sheets

U.S. PATENT DOCUMENTS

| | | | |
|---|---|---|---|
| 3,794,043 A | 2/1974 | McGinnis | |
| 3,815,606 A | 6/1974 | Mazal | |
| 3,834,383 A | 9/1974 | Weigl et al. | |
| 3,933,171 A | 1/1976 | Hay | |
| 3,973,564 A * | 8/1976 | Carden | 128/205.14 |
| 4,041,943 A | 8/1977 | Miller | |
| 4,077,404 A | 3/1978 | Elam | |
| 4,166,458 A | 9/1979 | Harrigan | |
| 4,226,233 A | 10/1980 | Kritzer | |
| 4,259,951 A | 4/1981 | Chernack et al. | |
| 4,298,023 A * | 11/1981 | McGinnis | 137/529 |
| 4,316,458 A | 2/1982 | Hammerton-Fraser | |
| 4,320,754 A | 3/1982 | Watson et al. | |
| 4,349,015 A | 9/1982 | Alferness | |
| 4,397,306 A * | 8/1983 | Weisfeldt et al. | 601/41 |
| 4,446,864 A | 5/1984 | Watson et al. | |
| 4,449,526 A | 5/1984 | Elam | |
| 4,481,938 A | 11/1984 | Lindley | |
| 4,533,137 A * | 8/1985 | Sonne | 482/13 |
| 4,601,465 A * | 7/1986 | Roy | 482/13 |
| 4,809,683 A | 3/1989 | Hanson | |
| 4,827,935 A | 5/1989 | Geddes et al. | |
| 4,881,527 A * | 11/1989 | Lerman | 601/44 |
| 4,898,166 A | 2/1990 | Rose et al. | |
| 4,928,674 A * | 5/1990 | Halperin et al. | 601/44 |
| 4,971,042 A * | 11/1990 | Lerman | 601/44 |
| 5,014,698 A | 5/1991 | Cohen | |
| 5,016,627 A | 5/1991 | Dahrendorf | |
| 5,050,593 A | 9/1991 | Poon | |
| 5,056,505 A * | 10/1991 | Warwick et al. | 601/44 |
| 5,109,840 A | 5/1992 | Daleidon | |
| 5,163,424 A * | 11/1992 | Kohnke | 128/205.13 |
| 5,184,620 A | 2/1993 | Cudahy et al. | |
| 5,193,544 A | 3/1993 | Jaffe | |
| 5,217,006 A | 6/1993 | McCulloch | |
| 5,235,970 A | 8/1993 | Augustine | |
| 5,263,476 A | 11/1993 | Henson | |
| 5,295,481 A | 3/1994 | Geeham | |
| 5,301,667 A | 4/1994 | McGrail et al. | |
| 5,305,743 A | 4/1994 | Brain | |
| 5,316,907 A | 5/1994 | Lurie | |
| 5,355,879 A | 10/1994 | Brain | |
| 5,359,998 A | 11/1994 | Lloyd | |
| 5,377,671 A | 1/1995 | Biondi et al. | |
| 5,392,774 A | 2/1995 | Sato | |
| 5,398,714 A * | 3/1995 | Price | 137/102 |
| 5,423,772 A | 6/1995 | Lurie | |
| 5,454,779 A | 10/1995 | Lurie et al. | |
| 5,474,533 A * | 12/1995 | Ward et al. | 604/26 |
| 5,492,115 A * | 2/1996 | Abramov et al. | 128/205.24 |
| 5,492,116 A | 2/1996 | Scarberry et al. | |
| 5,496,257 A | 3/1996 | Kelly | |
| 5,517,986 A | 5/1996 | Starr et al. | |
| 5,549,581 A | 8/1996 | Lurie | |
| 5,551,420 A | 9/1996 | Lurie et al. | |
| 5,588,422 A | 12/1996 | Lurie | |
| 5,618,665 A | 4/1997 | Lurie | |
| 5,628,305 A | 5/1997 | Melker | |
| 5,632,298 A | 5/1997 | Artinian | |
| 5,643,231 A | 7/1997 | Lurie | |
| 5,645,522 A | 7/1997 | Lurie et al. | |
| 5,678,535 A * | 10/1997 | DiMarco | 128/200.24 |
| 5,692,498 A | 12/1997 | Lurie et al. | |
| 5,704,346 A | 1/1998 | Inoue | |
| 5,722,963 A | 3/1998 | Lurie | |
| 5,730,122 A | 3/1998 | Lurie | |
| 5,735,876 A | 4/1998 | Kroll et al. | |
| 5,738,637 A * | 4/1998 | Kelly et al. | 601/41 |
| 5,782,883 A | 7/1998 | Kroll et al. | |
| 5,814,086 A | 9/1998 | Hirschberg et al. | |
| 5,823,185 A * | 10/1998 | Chang | 128/204.18 |
| 5,827,893 A | 10/1998 | Lurie | |
| 5,896,857 A * | 4/1999 | Hely et al. | 128/205.24 |
| 5,919,210 A | 7/1999 | Lurie | |
| 5,984,909 A | 11/1999 | Lurie | |
| 5,988,166 A * | 11/1999 | Hayek | 128/205.26 |
| 6,001,085 A | 12/1999 | Lurie | |
| 6,029,667 A | 2/2000 | Lurie | |
| 6,062,219 A | 5/2000 | Lurie et al. | |
| 6,078,834 A | 6/2000 | Lurie | |
| 6,155,257 A | 12/2000 | Lurie et al. | |
| 6,224,562 B1 | 5/2001 | Lurie et al. | |
| 6,234,985 B1 | 5/2001 | Lurie et al. | |
| 6,277,107 B1 | 8/2001 | Lurie | |
| 6,312,399 B1 | 11/2001 | Lurie et al. | |
| 6,425,393 B1 | 7/2002 | Lurie et al. | |
| 6,459,933 B1 | 10/2002 | Lurie et al. | |
| 6,463,327 B1 | 10/2002 | Lurie et al. | |
| 6,486,206 B1 | 11/2002 | Lurie | |
| 6,526,973 B1 | 3/2003 | Lurie et al. | |
| 6,578,574 B1 | 6/2003 | Kohnke | |
| 6,587,726 B2 | 7/2003 | Lurie et al. | |
| 6,604,523 B2 | 8/2003 | Lurie et al. | |
| 6,615,257 B2 | 9/2003 | Lee et al. | |
| 6,656,166 B2 | 12/2003 | Lurie | |
| 6,776,156 B2 | 8/2004 | Lurie et al. | |
| 6,792,947 B1 | 9/2004 | Bowden | |
| 6,863,656 B2 | 3/2005 | Lurie | |
| 6,935,336 B2 | 8/2005 | Lurie et al. | |
| 6,938,618 B2 | 9/2005 | Lurie et al. | |
| 6,986,349 B2 | 1/2006 | Lurie | |
| 2001/0029399 A1 | 10/2001 | Orr et al. | |
| 2002/0069878 A1 | 6/2002 | Lurie et al. | |
| 2002/0170562 A1 | 11/2002 | Lurie et al. | |
| 2003/0000526 A1* | 1/2003 | Gobel | 128/204.18 |
| 2003/0037784 A1 | 2/2003 | Lurie | |
| 2003/0062040 A1 | 4/2003 | Lurie | |
| 2003/0062041 A1 | 4/2003 | Lurie et al. | |
| 2003/0192547 A1 | 10/2003 | Lurie et al. | |
| 2004/0200473 A1 | 10/2004 | Lurie | |
| 2004/0200474 A1 | 10/2004 | Lurie | |
| 2004/0211415 A1 | 10/2004 | Lurie et al. | |
| 2004/0211416 A1 | 10/2004 | Lurie | |
| 2004/0211417 A1 | 10/2004 | Lurie | |
| 2004/0231664 A1 | 11/2004 | Lurie | |
| 2005/0126567 A1 | 6/2005 | Lurie et al. | |
| 2005/0165334 A1 | 7/2005 | Lurie et al. | |
| 2005/0199237 A1 | 9/2005 | Lurie et al. | |
| 2005/0217677 A1 | 10/2005 | Lurie | |
| 2005/0267381 A1 | 12/2005 | Benditt | |

FOREIGN PATENT DOCUMENTS

| | | |
|---|---|---|
| CA | 2077608 A1 | 3/1993 |
| DE | 24 53 490 A1 | 5/1975 |
| EP | 0 029 352 A1 | 5/1981 |
| EP | 0 139 363 A1 | 5/1985 |
| EP | 0 245 142 A1 | 11/1987 |
| EP | 0 367 285 B1 | 5/1990 |
| EP | 0 411 714 A1 | 2/1991 |
| EP | 0 509 773 A1 | 10/1992 |
| GB | 1 465 127 | 2/1977 |
| GB | 2 139 099 A | 11/1984 |
| WO | WO90/05518 A1 | 5/1990 |
| WO | WO93/21982 A1 | 11/1993 |
| WO | WO94/26229 A1 | 11/1994 |
| WO | WO95/13108 A1 | 5/1995 |
| WO | WO95/28193 A1 | 10/1995 |
| WO | WO96/28215 A1 | 9/1996 |
| WO | WO99/63926 A1 | 12/1999 |
| WO | WO01/70332 A1 | 9/2001 |

WO    WO02/092169 A1    11/2002

OTHER PUBLICATIONS

Cohen, Todd J. et al., "Active Compression-Decompression Resuscitation: a Novel Method of Cardiopulmonary Resuscitation", Department of Medicine and the Cardiovascular Research Institute, UC San Francisco, American Heart Journal 126(5):1145-1150, 1992.

Dupuis, Yvon G., *Ventilators—Theory and Clinical Application*, pp. 447-448, 481, 496; Jan. 1986, Mosby Company.

Geddes, L.A. et al., "Inspiration Produced by Bilateral Electromagnetic, Cervical Phrenic Nerve Stimulation In Man," IEEE Transactions on Biomedical Engineering 38(9): 1047-1048 (Oct. 1991).

Geddes, L.A. et al., "Optimum Stimulus Frequency for Contracting the Inspiratory Muscles with chest Surface Electrodes to Produce Artificial respiration," Annals of Biomedical Engineering 18:103-108 (1990).

Geddes, L.A., "Electrically Produced Artificial Ventilation," Medical Instrumentation 22(5): 263-271 (1988).

Geddes, L.A. "Electroventilation—A Missed Oppurtunity?", Biomedical Instrumentation & Technology, Jul./Aug. 1998, pp. 401-414.

Glenn, William W.L. et al., "Diaphragm Pacing by Electrical Stimulation of the Phrenic Nerve," Neurosurgery 17(6): 974-984 (1985).

Glenn, William W.L., et al., "Twenty Years of Experience in Phrenic Nerve Stimulation to Pace the Diaphragm," Pace 9: 780-784 (Nov./Dec. 1986, Part I).

Kotze, P.L. et al., "Diaphragm Pacing in the Treatment of Ventilatory Failure," San. Deel 68:223-224 (Aug. 17, 1995).

Laghi, Franco et al., "Comparison of Magnetic and Electrical Phrenic Nerve Stimulation in assessment of Diaphragmantic Contractility," American Physiological society, pp. 1731-1742 (1996).

Lindner, Karl H. et al., "Effects of Active Compression-Decompression Resuscitation on Myocardial and Cerebral Blood Flow in Pigs" Department of Anesthesiology and Critical Care Medicine, University of Ulm, Germany, Circulation 88(3):1254-1263, (Oct. 7, 1993).

Lurie, Keith G. et al., "Regulated to Death: The Matter of Informed Consent for Human Experimentation in Emergency Resuscitation Research," Cardiac Arrhythmia Center at the University of Minnesota, PACE 18:1443-1447(Jul. 1995).

Mushin W. W. et al., "Automatic Ventilation of the Lungs—The Lewis-Leigh Inflating Valve," Blackwell Scientific, Oxford, GB, p. 838.

U.S. Appl. No. 10/119,203, filed Apr. 8, 2002, Lurie et al.
U.S. Appl. No. 10/396,007, filed Mar. 24, 2003, Lurie et al.
U.S. Appl. No. 10/401,493, filed Mar. 28, 2003, Lurie.
U.S. Appl. No. 10/410,229, filed Apr. 8, 2003, Lurie et al.
U.S. Appl. No. 10/426,161, filed Apr. 28, 2003, Lurie.
U.S. Appl. No. 10/460,558, filed Jun. 11, 2003, Lurie.
U.S. Appl. No. 10/660,462, filed Sep. 11, 2003, Lurie.
U.S. Appl. No. 10/765,318, filed Jan. 26, 2004, Lurie.
U.S. Appl. No. 10/796,875, filed Mar. 8, 2004, Lurie et al.
U.S. Appl. No. 11/034,996, filed Jan. 12, 2005, Lurie.
U.S. Appl. No. 11/127,993, filed May 11, 2005, Lurie et al.
U.S. Appl. No. 11/051,345, filed Feb. 4, 2005, Lurie.
US 5,584,866, 12/1996, Kroll et al. (withdrawn)

* cited by examiner

SYSTEMS AND METHODS FOR INCREASING CEREBRAL SPINAL FLUID FLOW

CROSS REFERENCE TO RELATED APPLICATIONS

This application is a continuation-in-part of U.S. patent application Ser. No. 10/426,161, filed Apr. 28, 2003, the complete disclosure of which is herein incorporated by reference.

BACKGROUND OF THE INVENTION

This invention relates generally to the field of intracranial and intraocular pressures. More specifically, the invention relates to devices and methods for decreasing intracranial and intraocular pressures, such as those resulting from a traumatic head injury.

Head trauma is generally regarded as the leading cause of morbidity and mortality in the United States for children and young adults. Head trauma often results in swelling of the brain. Because the skull cannot expand, the increased pressures within the brain can lead to death or serious brain injury. While a number of therapies have been evaluated in order to reduce brain selling, including use of hyperventilation and steroids, an effective way to treat intracranial pressures remains an important medical challenge.

BRIEF SUMMARY OF THE INVENTION

In one embodiment, the invention provides a device for decreasing intracranial or intraocular pressures. The device comprises a housing having an inlet opening and an outlet opening that is adapted to be interfaced with a person's airway. The device further includes a valve system that is operable to regulate respiratory gas flows through the housing and into the person's lungs during spontaneous or artificial inspiration. The valve system assists in lowering intrathoracic pressures during inspiration to continuously or intermittently lower pressures in the venous blood vessels that transport blood out of the head to thereby reduce intracranial or intraocular pressures.

Such a device may also be used to facilitate movement of cerebral spinal fluid. In so doing, intracranial pressures may be further reduced. Such a device may therefore be used to treat those suffering from head trauma associated with elevated intracranial pressures as well as those suffering from heart conditions that increase intracranial pressures.

In one aspect, the valve system is configured to open to permit respiratory gasses to freely flow to the person's lungs when the negative intrathoracic pressure reaches a pressure in the range from about −2 cmH2O to about −20 cmH2O in order to reduce intracranial or intraocular pressures. In this way, the negative intrathoracic pressure is lowered until a threshold pressure is reached, at which time the valve opens. The cycle may be repeated continuously or periodically to repetitively lower intrathoracic pressures.

The device may also include means for causing the person to artificially inspire through the valve system. For example, the device may utilize an electrode, an iron lung cuirass device, a chest lifting device, a ventilator or the like.

In another embodiment, the device may comprise a means to reduce intrathoracic pressure by applying a vacuum within the airway. The vacuum may be adjusted in terms of frequency, amplitude, and duration. This results in a decrease in intracranial pressure in proportion to the degree of vacuum applied. Hence, intracranial pressures may be reduced simply by manipulating airway pressures to reduce intrathoracic pressures.

The device may further include a mechanism for varying the level of impedance of the valve system. This may be used in combination with at least one physiological sensor that is configured to monitor at least one physiological parameter of the person. In this way, the mechanism for varying the level of impedance may be configured to receive signals from the sensor and to vary the level of impedance of the valve system based on the signals. Examples of sensors that may be used include those that measure respiratory rate, intrathoracic pressure, intratracheal pressure, blood pressure, heart rate, end tidal CO2, oxygen level, intracranial perfusion, and intracranial pressure.

In one aspect, a coupling mechanism may be used to couple the valve system to the person's airway. Examples of coupling mechanisms include a mouthpiece, an endotracheal tube, and a face mask.

A wide variety of valve systems may be used to repetitively decrease the person's intrathoracic pressure. For example, valve systems that may be used include those having spring-biased devices, those having automated, electronic or mechanical systems to occlude and open a valve lumen, duck bill valves, ball valves, other pressure sensitive valve systems capable of opening a closing when subjected to low pressure differentials triggered either by spontaneous breathing and/or external systems to manipulate intrathoracic pressures (such as ventilators, phrenic nerve stimulators, iron lungs, and the like).

In another embodiment, the invention provides a method for decreasing intracranial or intraocular pressures. According to the method, a valve system is coupled to a person's airway and is configured to at least periodically reduce or prevent respiratory gases from flowing to the person's lungs. With the valve system coupled to the airway, the person's negative intrathoracic pressure is repetitively decreased to in turn repetitively lower pressures in the venous blood vessels that transport blood out of the head. In so doing, intracranial and intraocular pressures are reduced. Such a method also facilitates movement of cerebral spinal fluid. In so doing, intracranial pressures are further reduced. As such, this method may also be used to treat a person suffering from head trauma that is associated with elevated intracranial pressures as well as those suffering from heart conditions that increase intracranial pressures, such as atrial fibrillation and heart failure.

The person's negative intrathoracic pressure may be repetitively decreased as the person repeatedly inspires through the valve system. This may be done by the person's own efforts (referred to as spontaneous breathing), or by artificially causing the person to repeatedly inspire through the valve system. For example, the person may be caused to artificially inspire by repeatedly stimulating the phrenic nerve, by manipulating the chest with an iron lung cuirass device, by generating negative pressures within the thorax using a ventilator, by applying a high frequency ventilator that supplies oscillations at a rate of about 200 to about 2000 per minute, or the like.

In another aspect, the level of impedance of the valve system may be fixed or variable. If variable, at least one physiological parameters of the person may be measured, and the impedance level may be varied based on the measured parameters.

To couple the valve system to the airway, a variety of techniques may be used, such as by using a mouthpiece, an endotracheal tube, a face mask or the like. Further, the respiratory gases may be prevented from entering the lungs through the valve system until a negative intrathoracic pressure in the range from about 0 cmH2O to about −25 cmH2O is achieved, at which time the valve system permits respiratory gases to flow to the lungs.

DETAILED DESCRIPTION OF THE INVENTION

Figure 1:
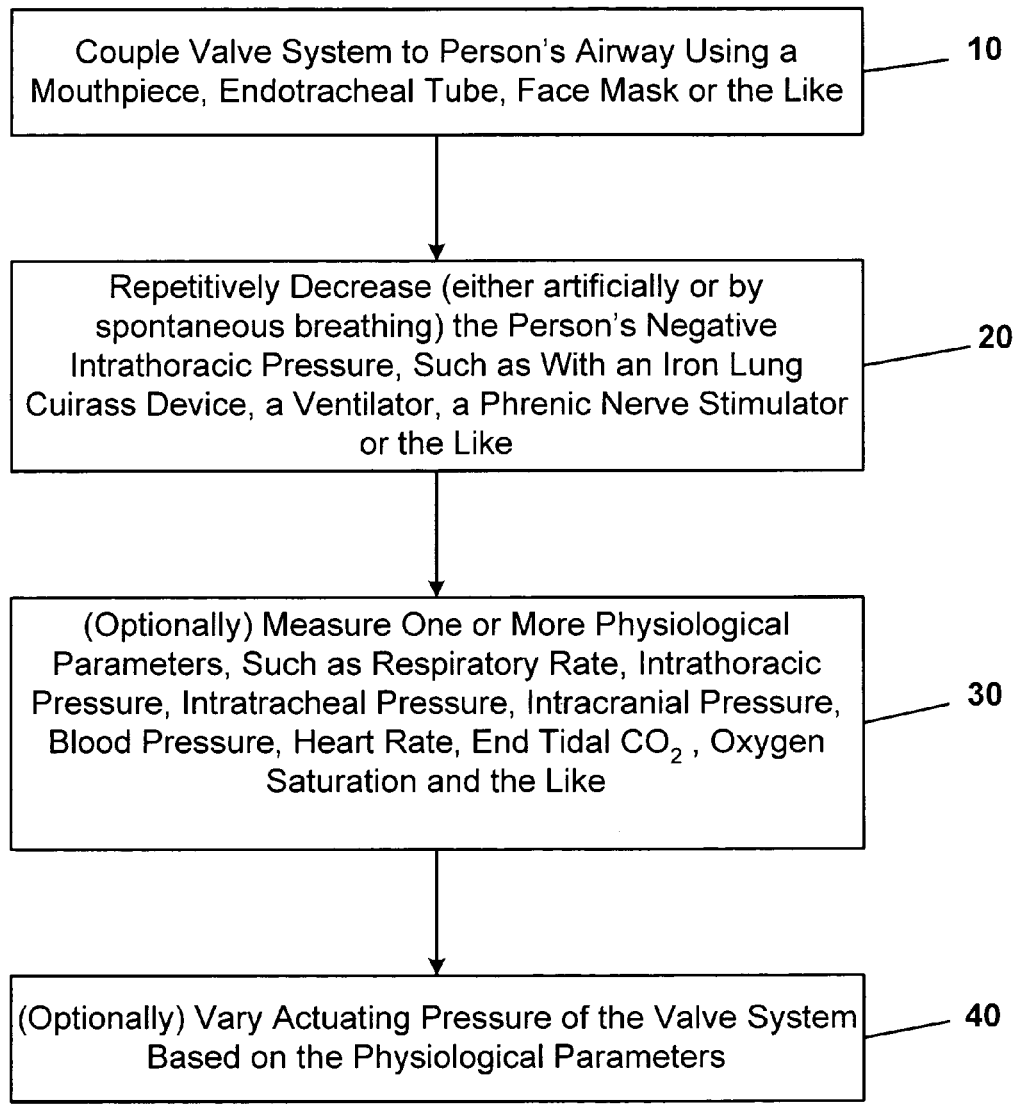
FIG. 1 is a flow chart illustrating one method for reducing intracranial and intraocular pressures according to the invention.

In a broad sense, the invention provides devices and techniques for lowering intracranial and intraocular pressures. Such devices and techniques may be particularly helpful with patients who have suffered a traumatic brain injury. One way to lower such pressures is by using a valve system that is coupled to a person's airway and that is used to lower intrathoracic pressures. In so doing, the valve systems may be used to accelerate the removal of venous blood from the brain, thereby decreasing intracranial and intraocular pressures. Other techniques may be used as well, such as by creating a vacuum intermittently within the thorax. By reducing intracranial pressures, movement of cerebral spinal fluid is also enhanced. In so doing, intracranial pressures are further reduced thereby providing further treatment for those suffering from head trauma. In some cases, the valve systems may also be used to treat the brain function in a person suffering from a heart condition (atrial fibrillation, heart failure, cardiac tamponade, and the like) that results in elevated intracranial pressures. Such heart conditions may include, for example, atrial fibrillation or heart failure. By reducing intracranial pressures, cerebral spinal fluid movement and translocation is increased to help improve brain function.

Intracranial pressures are regulated by the amount the cerebral perfusion pressure, which is determined by the arterial blood pressure to the head, the pressures within the skull, and the pressures within the venous system that drains blood flow from the brain. The devices and methods of the invention may be used to enhance the egress of venous blood out of the brain, thereby lowering intracranial pressures. To do so, the devices and methods may be used to augment the intrathoracic vacuum effect each time a patient inhales (or in the case of a non-breathing patient, each time the pressure within the chest is manipulated to fall below atmospheric pressure), thereby lowering the pressures in the thorax and in the venous blood vessels that transport blood out of the brain. The vacuum effect is transduced back into the brain, and as a result, intracranial pressures are lowered with each inspiratory effort. This in turn causes more venous blood to flow out of the head than would otherwise be possible, resulting in lower intracranial pressures and lower intraocular pressures.

To prevent or impede respiratory gases from flowing to the lungs, a variety of impeding or preventing mechanisms may be used, including those described in U.S. Pat. Nos. 5,551,420; 5,692,498; 6,062,219; 5,730,122; 6,155,257; and 6,224,562, and in U.S. patent application Ser. No. 10/224,263, filed on Aug. 19, 2002 ("Systems and Methods for Enhancing Blood Circulation", U.S. patent application Ser. No. 10/401,493, filed Mar. 28, 2003 ("Diabetes Treatment Systems and Methods"), U.S. patent application Ser. No. 09/966,945, ("Face Mask Ventillation/Perfusion Systems & Method"), filed Sep. 28, 2001 and U.S. patent application Ser. No. 09/967,029, ("Systems and Methods to Facilitate the Delivery of Drugs"), filed Sep. 28, 2001, the complete disclosures of which are herein incorporated by reference. The valve systems may be configured to completely prevent or provide resistance to the inflow of respiratory gases into the patient while the patient inspires. For valve systems that completely prevent the flow of respiratory gases, such valves may be configured as pressure responsive valves that open after a threshold negative intrathoracic pressure has been reached.

For example, the resistance to the inflow of respiratory gases may be set between about 0 cm H2O and about −25 cm H2O and may be variable or fixed. More preferably, the valve system may be configured to open when the negative intrathoracic pressure is in the range from about −2 cmH2O to about −20 cmH2O.

Although not intended to be limiting, specific kinds of impedance valves that may be used to reduce intracranial and intraocular pressures include those having spring-biased devices, automated/electronic and mechanical means to occlude and open a valve lumen, duck bill valves, ball valves, and other pressure sensitive valve systems capable of opening and closing when subjected to low pressure differentials triggered either by spontaneous breathing and/or external means to manipulate intrathoracic pressure (such as ventilators, phrenic nerve stimulators, an iron lung, and the like).

In the past, such threshold valve systems have been used to increase the venous preload on the heart and to increase cardiac output, stroke volume and blood pressure because of the augmented effects of the intrathoracic vacuum on the subsequent cardiac contraction. In contrast, the techniques of the invention function by facilitating the removal of blood from the venous side of the brain. Although there may be an increase in blood flow out of the heart to the vital organs (including to the brain) when using such valve systems, the effect of the valve systems on lowering of intracranial pressures was quite unexpected because of the known increase in blood flow to the brain. Remarkably, however, the reduction of venous blood pressures from the brain remains substantial when using the valve systems. Thus, despite the increase in blood flow to the brain, the net effect of the valve system is a decrease in intracranial pressures.

With the valve system coupled to the person's airway, the negative intrathoracic pressure may be enhanced by inspiring through the valve system. If the person is spontaneously breathing, the person may simply breath through the valve system. If the person is not breathing, artificial inspiration may be induced using a variety of techniques, including electrical stimulation of the diaphragm, a negative pressure ventilator such as a body cuirass or iron lung, or a positive pressure ventilator capable of also generating a vacuum between positive pressure ventilations. As one example, at least some of the respiratory muscles, and particularly the inspiratory muscles, may be stimulated to contract in a repeating manner in order to cause the person to inspire through the valve system, thereby increasing the magnitude and prolonging the duration of negative intrathoracic pressure, i.e., respiratory muscle stimulation increases the duration and degree that the intrathoracic pressure is below or negative with respect to the pressure in the peripheral venous vasculature. Upon contraction of the respiratory muscles, the patient will typically "gasp". These techniques may be performed alone, or in combination with a valve system.

Among the respiratory muscles that may be stimulated to contract are the diaphragm, the chest wall muscles, including the intercostal muscles and the abdominal muscles. Specific chest wall muscles that may be stimulated to contract include those that elevate the upper ribs, including the scaleni and stemocleidomastoid muscles, those that act to fix the shoulder girdle, including the trapezii, rhomboidei, and levatores angulorum scapulorum muscles, and those that act to elevate the ribs, including the serrati antici majores, and the pectorales majores and minores as described generally in Leslie A. Geddes, "Electroventilation—A Missed Opportunity?", Biomedical Instrumentation & Technology, July/August 1998, pp. 401–414, the complete disclosure of which is herein incorporated by reference. Of the respiratory muscles, the two hemidiaphragms and intercostal muscles appear to be the greatest contributors to inspiration and expiration. The respiratory muscles may be stimulated to contract in a variety of ways. For example, the diaphragm may be stimulated to contract by supplying electrical current or a magnetic field to various nerves or muscle bundles which when stimulated cause the diaphragm to contract. Similar techniques may be used to stimulate the chest wall muscles to contract. A variety of pulse trains, pulse widths, pulse frequencies and pulse waveforms may be used for stimulation. Further, the electrode location and timing of pulse delivery may be varied. In one particular aspect, an electrical current gradient or a magnetic field is provided to directly or indirectly stimulate the phrenic nerve.

To electrically stimulate the inspiratory motor nerves, electrodes are preferably placed on the lateral surface of the neck over the point where the phrenic nerve, on the chest surface just lateral to the lower sternum to deliver current to the phrenic nerves just as they enter the diaphragm, on the upper chest just anterior to the axillae to stimulate the thoracic nerves, in the oral pharyngeal region of the throat, or on the larynx itself. However, it will be appreciated that other electrode sites may be employed. For example, in one embodiment the respiratory muscles are stimulated by a transcutaneous electrical impulse delivered along the lower antero-lat margin of the rib cage. In one embodiment, inspiration is induced by stimulating inspiratory muscles using one or more electrodes attached to an endotracheal tube or pharyngeal tube. To stimulate the diaphragm, the phrenic nerve may be stimulated in the neck region near C3–C7, such as between C3, C4 or C5, or where the phrenic nerves enter the diaphragm. Alternative techniques for stimulating diaphragmatic contraction include magnetic field stimulation of the diaphragm or the phrenic nerve. Magnetic field stimulation may also be employed to stimulate the chest wall muscles. Electrical field stimulation of the diaphragm or the chest wall muscles may be accomplished by placing one or more electrodes on the skin, preferably in the vicinity of the neck or the lower rib cage (although other locations may be employed) and then providing an electrical voltage gradient between electrodes that induces transcutaneous current flow to stimulate the respiratory muscles to contract. Still further, subcutaneous electrodes may also be used to stimulate respiratory muscle contraction. Other techniques are described in U.S. Pat. No. 6,463,327, the complete disclosure of which is herein incorporated by reference.

The valve systems may have a fixed actuating pressure or may be variable so that once a desired negative intrathoracic pressure is reached, the resistance to flow may be lessened. Further, the valves of the invention may be configured to be variable, either manually or automatically. The extent to which the resistance to flow is varied may be based on physiological parameters measured by one or more sensors that are associated with the person being treated. As such, the resistance to flow may be varied so that the person's physiological parameters are brought within an acceptable range. If an automated system is used, such sensors may be coupled to a controller which is employed to control one or more mechanisms that vary the resistance or actuating pressure of the inflow valve as generally described in the references that have been incorporated by reference.

Hence, the valve systems of the invention may also incorporate or be associated with sensors that are used to detect changes in intrathoracic pressures or other physiological parameters. In one aspect, the sensors may be configured to wirelessly transmit their measured signals to a remote receiver that is in communication with a controller. In turn the controller may use the measured signals to vary operation of the valve systems described or incorporated by reference herein. For example, sensors may be used to sense blood pressure, pressures within the heart, intrathoracic pressures, positive end expiratory pressure, respiratory rate, intracranial pressures, intraocular pressures, respiratory flow, oxygen delivery, temperature, blood pH, end tidal $CO_2$, tissue $CO_2$, blood oxygen, cardiac output or the like. Signals from these sensors may be wirelessly transmitted to a receiver. This information may then be used by a controller to control the actuating pressure or the resistance of an inflow valve as described in the references incorporated herein by reference.

The techniques for reducing intracranial pressures may be used in a variety of settings. For example, the techniques may be used in person's who are spontaneously breathing, those who are not breathing but whose hearts are beating, and those in cardiac arrest. In the latter case, the techniques may use some means to create a vacuum intermittently within the thorax during the performance of CPR. This could be by using a valve system or some other type of pressure manipulation system. Further, such systems may be used in other settings as well, including when the person is breathing.

FIG. 1 is flow diagram illustrating one method for reducing intracranial or intraocular pressures. As shown in step 10, the process proceeds by coupling a valve system to the person's airway. Any kind of coupling mechanism may be used, such as by a mouthpiece, an endotracheal tube, a face mask, or the like. Further, any of the valve systems described or incorporated herein by reference may be used. In step 20, the person's negative intrathoracic pressure is repetitively decreased (either artificially or by spontaneous breathing). Examples of techniques to artificially reduce the negative intrathoracic pressure include use of an iron lung cuirass device, a ventilator that is capable of generating negative pressures, a ventilator that is capable of providing high frequency oscillations at a rate of about 200 to about 2000 per minute, a phrenic nerve stimulator, or the like. As the person's negative intrathoracic pressure is repeatedly decreased while the valve system is coupled to the airway, the pressures in the venous vessels that transport blood out of the head are also lowered. In so doing, intracranial and intraocular pressures are reduced.

As shown in step 30, various physiological parameters of the person may optionally be measured. Examples of such parameters include respiratory rate, intrathoracic pressure, intertracheal pressure, intracranial pressure, intracranial blood flow, intraocular pressure, blood pressure, heart rate, end tidal $CO_2$, oxygen saturation, and the like. Further, as shown in step 40, the valve system's actuating threshold level may optionally be varied based on the measured physiological parameters. This may be done to maximize the amount of blood drawn out of the brain or simply to monitor the patient's condition to insure that the patient remains stable.

Figure 2:
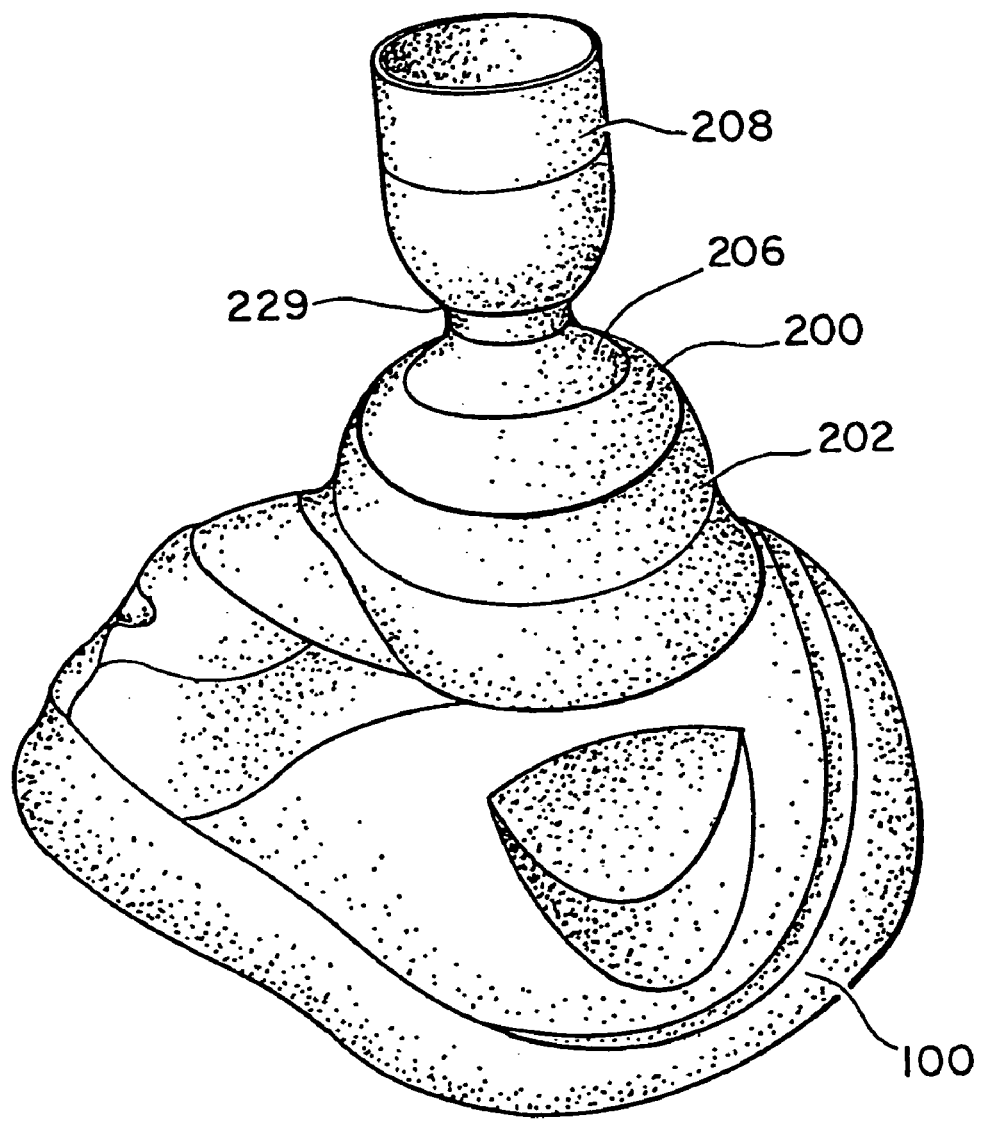
FIG. 2 is a perspective view of one embodiment of a facial mask and a valve system that may be used to reduce intracranial and intraocular pressures according to the invention.

FIG. 2 illustrates one embodiment of a facial mask 100 to which is coupled a valve system 200. Mask 100 is configured to be secured to a patient's face so as to cover the mouth and nose. Mask 100 and valve system 200 are examples of one type of equipment that may be used to lower intrathoracic pressures and thereby lower intracranial and intraocular pressures. However, it will be appreciated that other valve systems and other coupling arrangements may be used including, for example, those previously referenced. As such the invention is not intended to be limited to the specific valve system and mask described below.

Figure 3:
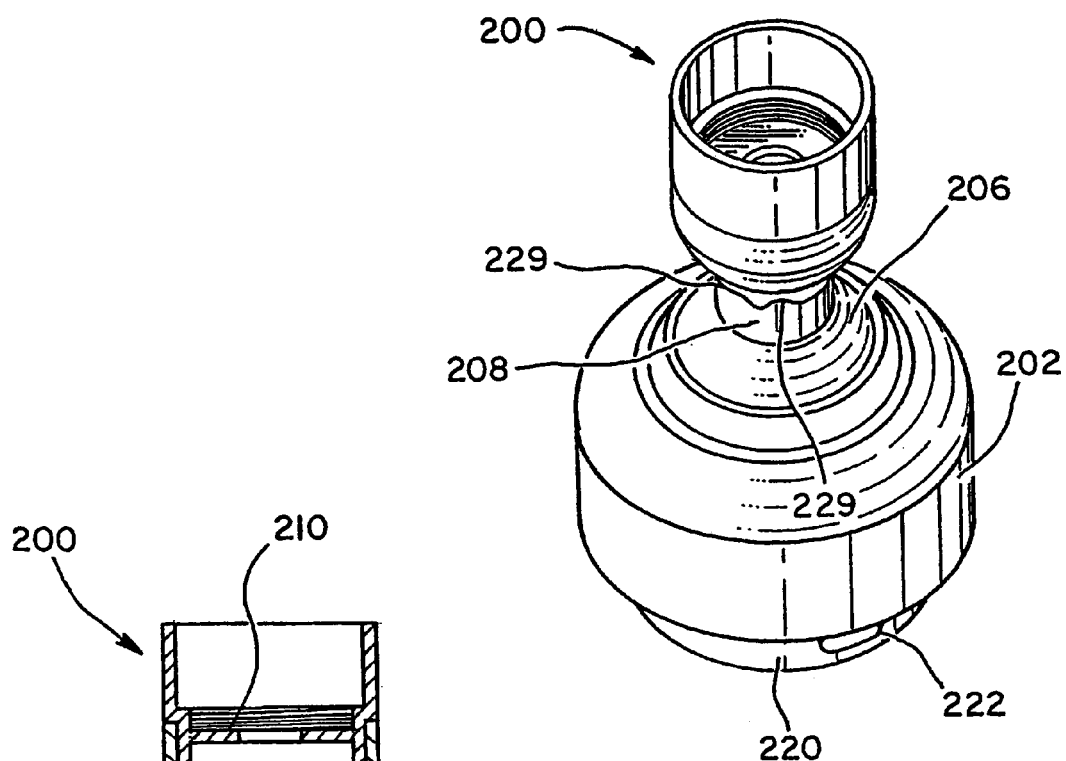
FIG. 3 is a perspective view of the valve system of FIG. 2.
Figure 4:
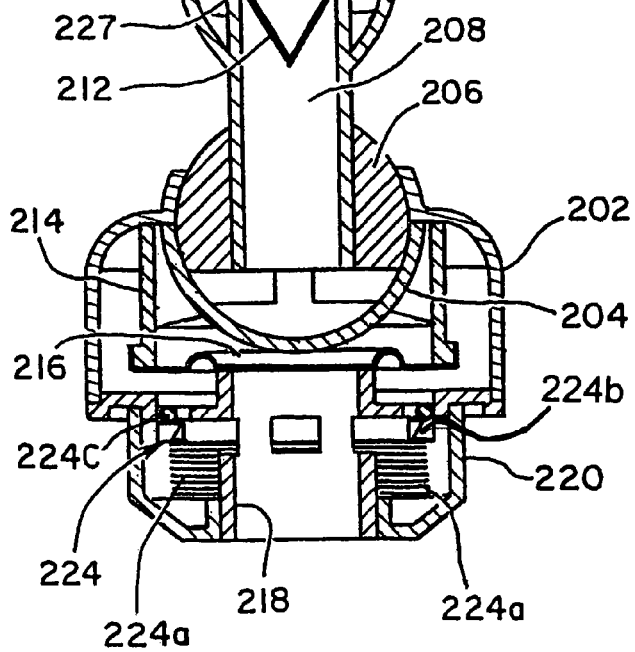
FIG. 4 is a cross sectional side view of the valve system of FIG. 3.
Figure 5:
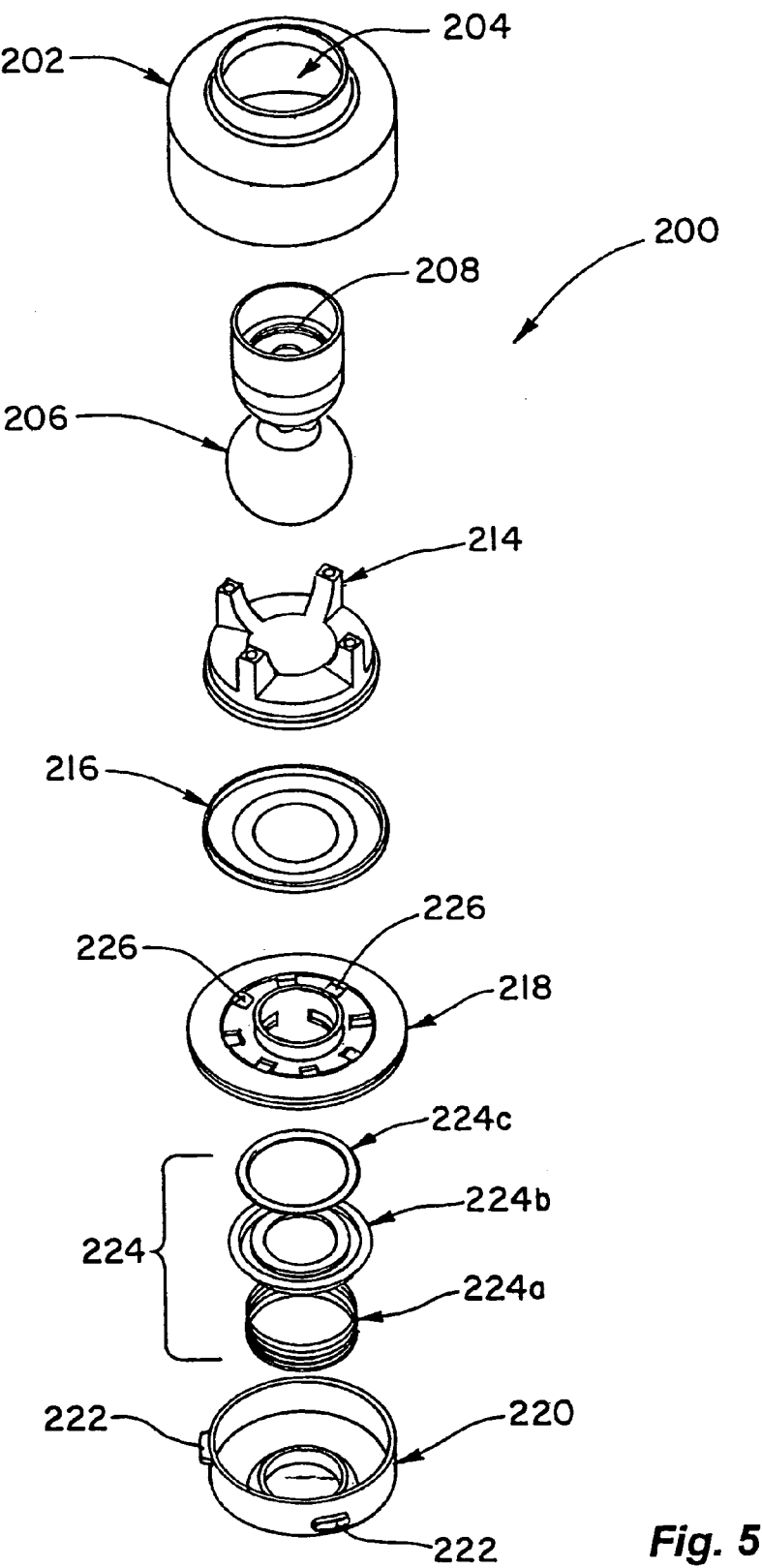
FIG. 5 is an exploded view of the valve system of FIG. 3.

Referring also to FIGS. 3–5, valve system 200 will be described in greater detail. Valve system 200 includes a valve housing 202 with a socket 204 into which a ball 206 of a ventilation tube 208 is received. In this way, ventilation tube 208 may rotate about a horizontal axis and pivot relative to a vertical axis. A respiratory source, such as a ventilation bag, may be coupled to tube 208 to assist in ventilation. Disposed in ventilation tube 208 is a filter 210 that is spaced above a duck bill valve 212. A diaphragm holder 214 that holds a diaphragm 216 is held within housing 202. Valve system 200 further includes a patient port 218 that is held in place by a second housing 220. Housing 220 conveniently includes tabs 222 to facilitate coupling of valve system 200 with facial mask 100. Also held within housing 220 is a check valve 224 that comprises a spring 224a, a ring member 224b, and an o-ring 224c. Spring 224a biases ring member 224b against patient port 218. Patient port 218 includes bypass openings 226 that are covered by o-ring 224c of check valve 224 until the pressure in patient port 218 reaches a threshold negative pressure to cause spring 224a to compress.

When the patient is actively ventilated, respiratory gases are forced through ventilation tube 208. The gases flow through filter 210, through duck bill valve 212, and forces up diaphragm 216 to permit the gases to exit through port 218. Hence, at any time the patient may be ventilated simply by forcing the respiratory gases through tube 208.

During the exhalation phase of a breathing cycle, expired gases flow through port 218 and lift up diaphragm 216. The gases then flow through a passage 227 in ventilation tube 208 where they exit the system through openings 229 (see FIG. 3).

During the inhalation phase of a breathing cycle, valve system 200 prevents respiratory gases from flowing into the lungs until a threshold negative intrathoracic pressure level is exceeded. When this pressure level is exceeded, check valve 224 is pulled downward as springs 224a are compressed to permit respiratory gases to flow through openings 226 and to the patient's lungs by initially passing through tube 208 and duck bill valve 212. Valve 224 may be set to open when the negative intrathoracic pressure is in the range from about 0 cm H2O to about −25 cm H2O, and more preferably from about −2 cm H2O to about −20 cm H2O. Hence, the magnitude and duration of negative intrathoracic pressure may be enhanced during patient inhalation by use of valve system 200. Once the intrathoracic pressure falls below the threshold, recoil spring 224a again close check valve 224. In this way, pressure within the venous blood vessels that transport blood out of the brain are also lowered. In so doing, more blood is drawn out of the brain to reduce intracranial and intraocular pressures.

Figure 6:
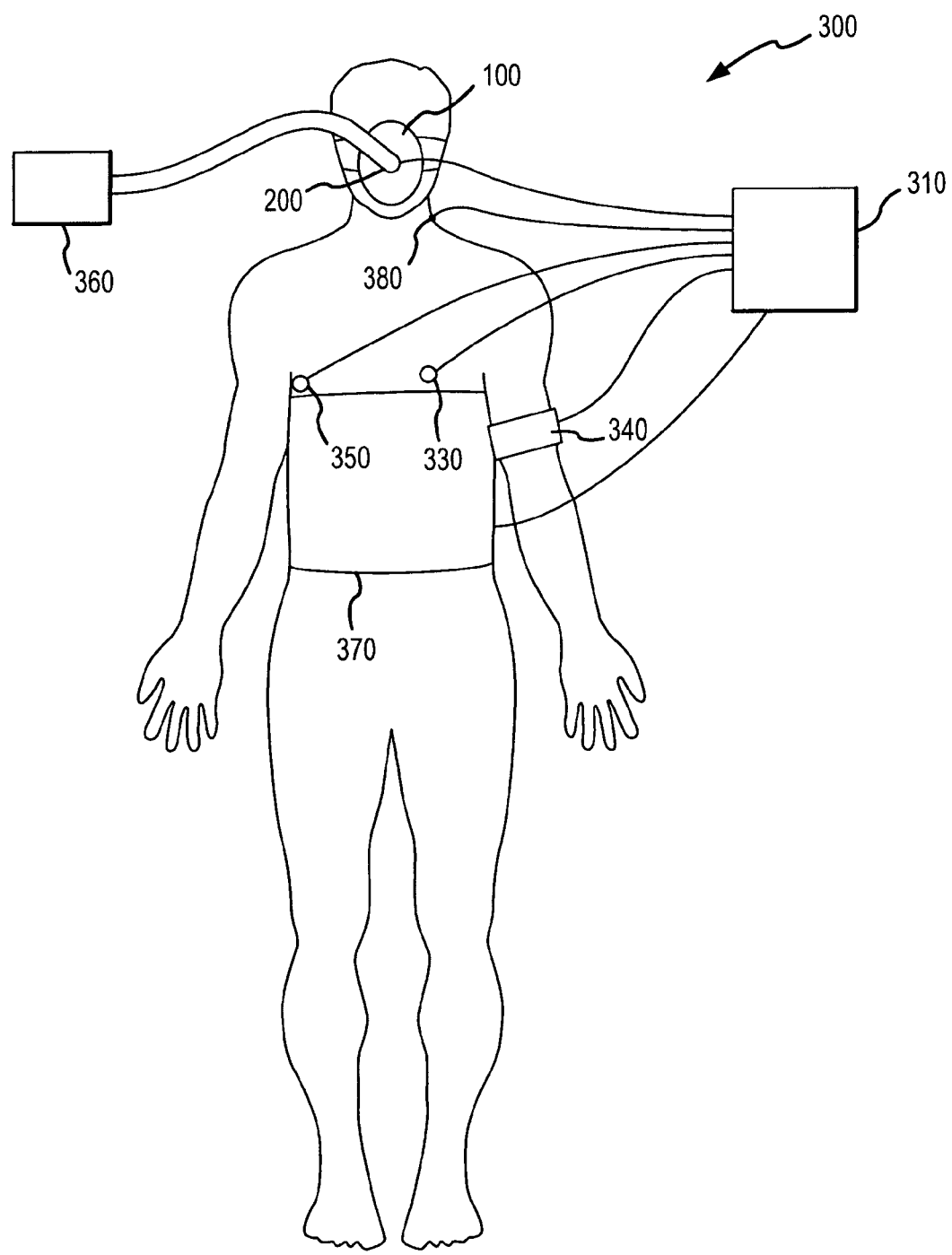
FIG. 6 is a schematic diagram of a system for reducing intracranial and intraocular pressures according to the invention.

Any of the valve systems described herein may be incorporated into a treatment system 300 as illustrated in FIG. 6. System 300 may conveniently include facial mask 100 and valve system 200, although any of the valve systems or interfacing mechanisms described herein or the like may be used. Valve system 200 may conveniently be coupled to a controller 310. In turn, controller 310 may be used to control the impedance level of valve system 200 in a manner similar to any of the embodiments described or incorporated herein. The level of impedance may be varied based on measurements of physiological parameters, or using a programmed schedule of changes. System 300 may include a wide variety of sensors and/or measuring devices to measure any of the physiological parameters described herein. These sensors or measuring devices may be integrated within or coupled to valve system 200 or facial mask, or may be separate.

For example, valve system 200 may include a pressure transducer for taking pressure measurements (such as intrathoracic pressures, intracranial pressures, intraocular pressures), a flow rate measuring device for measuring the flow rate of air into or out of the lungs, or a CO2 sensor for measuring expired CO2.

Examples of other sensors or measuring devices include a heart rate sensor 330, a blood pressure sensor 340, and a temperature sensor 350. These sensors may also be coupled to controller 310 so that measurements may be recorded. Further, it will be appreciated that other types of measuring devices may be used to measure various physiological parameters, such as oxygen saturation and/or blood levels of O2, blood lactate, blood pH, tissue lactate, tissue pH, blood pressure, pressures within the heart, intrathoracic pressures, positive end expiratory pressure, respiratory rate, intracranial pressures, intraocular pressures, respiratory flow, oxygen delivery, temperature, end tidal CO2, tissue CO2, cardiac output or the like.

In some cases, controller 310 may be used to control valve system 200, to control any sensors or measuring devices, to record measurements, and to perform any comparisons. Alternatively, a set of computers and/or controllers may be used in combination to perform such tasks. This equipment may have appropriate processors, display screens, input and output devices, entry devices, memory or databases, software, and the like needed to operate system 300.

A variety of devices may also be coupled to controller 310 to cause the person to artificially inspire. For example, such devices may comprise a ventilator 360, an iron lung cuirass device 370 or a phrenic nerve stimulator 380. Ventilator 360 may be configured to create a negative intrathoracic pressure within the person, or may be a high frequency ventilator capable of generating oscillations at about 200 to about 2000 per minute.

EXAMPLE 1

The following is a non-limiting example illustrating how intracranial pressures may be lowered according to the invention. In this example, 30 kg pigs were anesthetized with propofol. Using a micromannometer-tipped electronic Millar catheter inserted below the dura, intracranial pressures were measured continuously in the spontaneously breathing pigs. Intrathoracic pressures (ITP) were recorded using a Millar catheter placed in the trachea at the level of the carina. After stabilizing the pigs blood pressure, heart rate, and ventilation rate, intracranial pressures (ICP) and intrathoracic pressures were recorded, with 0 cmH2O inspiratory impedance and then with inspiratory impedances of 5, 10, 15, and 20 cm H2O. Inspiratory impedance was achieved using an impedance threshold valve (ITV) as described in FIGS. 2–5.

Figure 7:
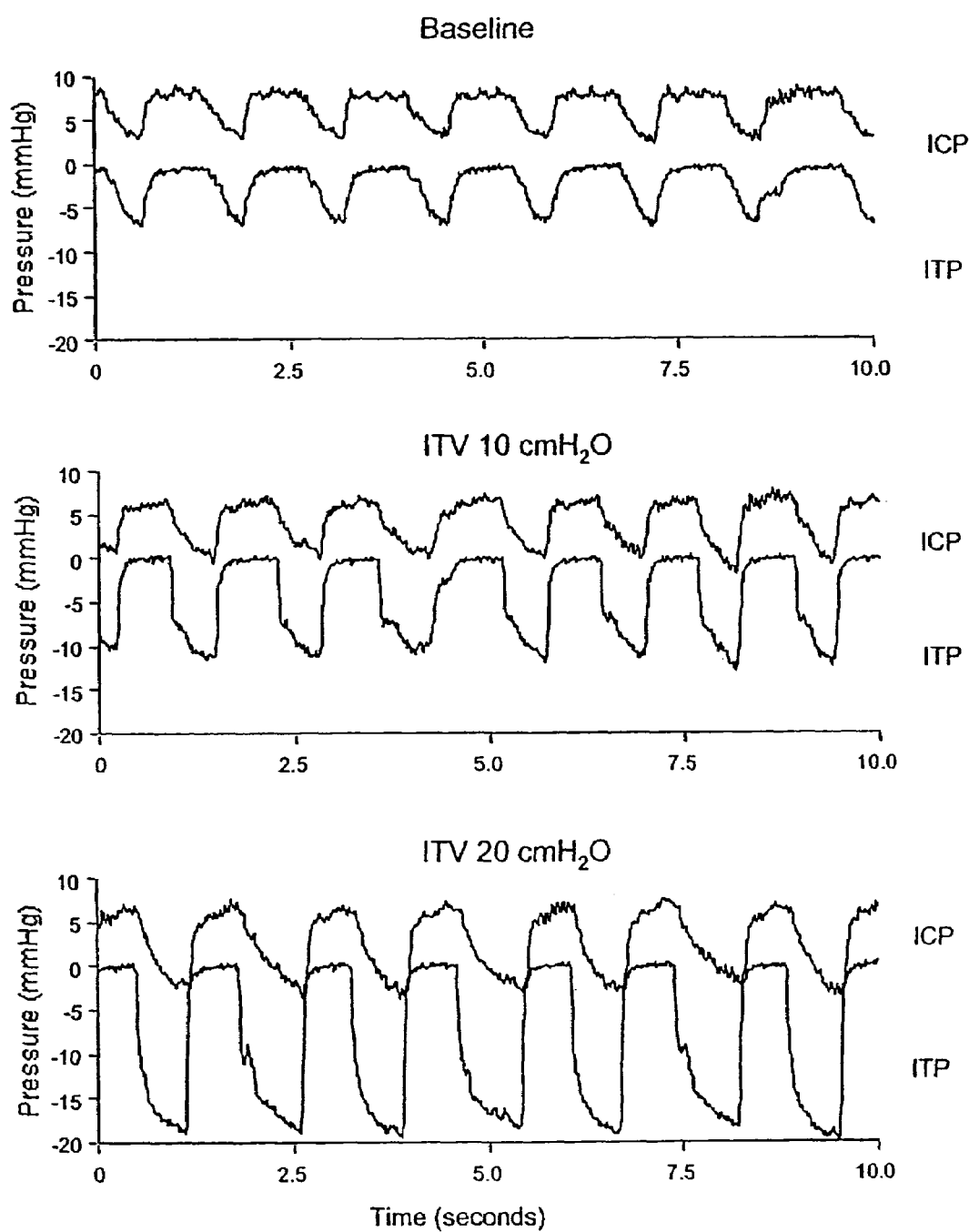
FIG. 7 is a series of graphs illustrating the lowering of intracranial pressures in an animal study.
Figure 8:
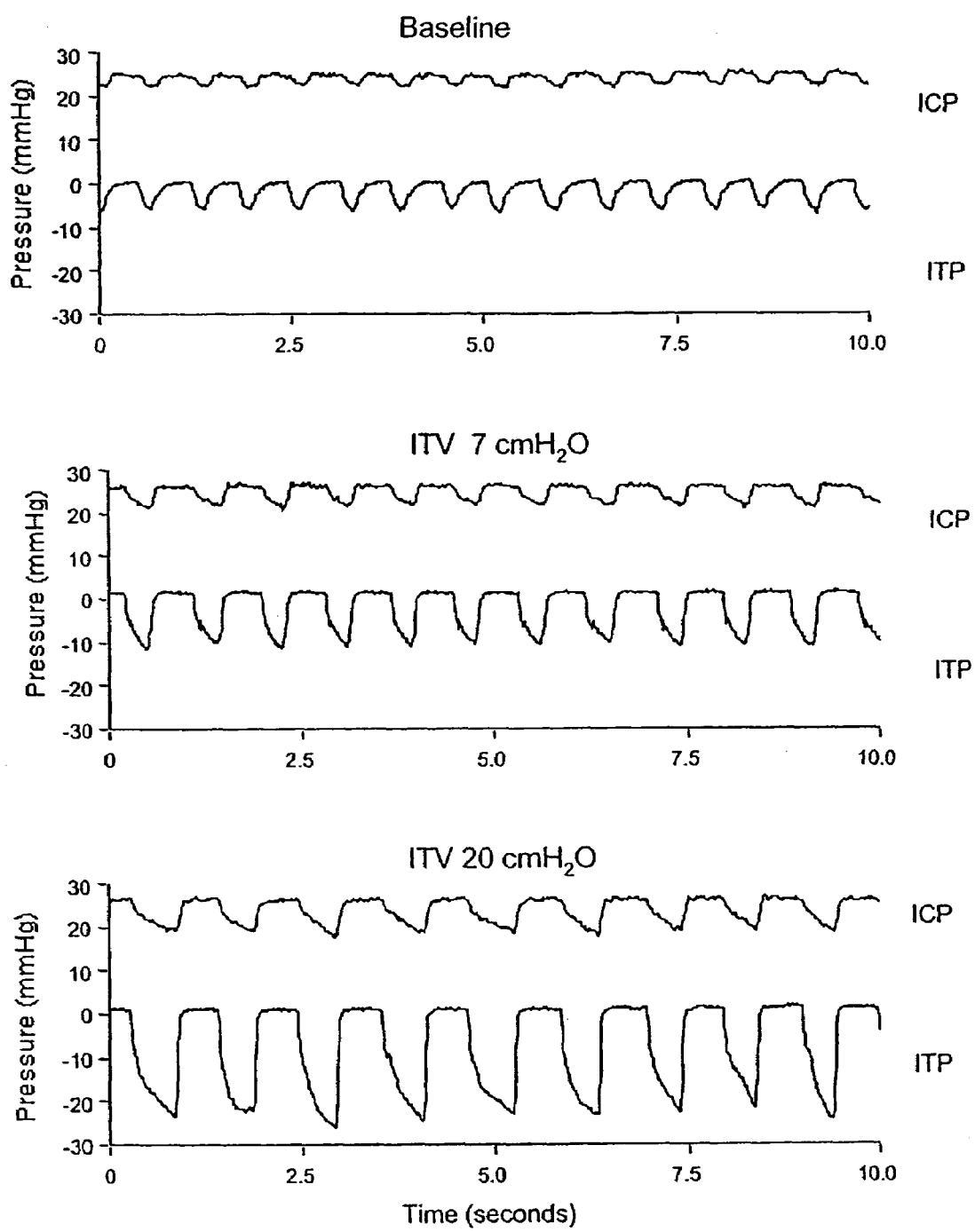
FIG. 8 is a series of graphs illustrating the lowering of intracranial pressures in another animal study.

At base, the intracranial pressure was approximately 8/4 mmHg. With increasing amounts of inspiratory impedance, the intracranial pressure was lowered proportionally as shown in FIG. 7. The intracranial pressure was 6/−2 mmHg when the pig breathed through an impedance of 20 cm H2O. These findings were observed in multiple pig studies and were reproducible. Next, the Millar catheter was inserted 3 cm into the pig's brain. The intracranial pressure increased secondary to the trauma associated with the insertion of the probe. The intracranial pressure increased to 25/22 mmHg at the new baseline. Next, the impedance threshold valve was evaluated at different levels of resistance (FIG. 8). Again, there was a decrease in intracranial pressure proportional to the degree of inspiratory impedance.

EXAMPLE 2

In this example, intracranial pressures were increased in the setting of recovery from cardiac arrest. The example used a pig model with ventricular fibrillation for 6 minutes followed by cardiopulmonary resuscitation for 6 minutes, followed by defibrillation. Spontaneous breathing resulted in an up to 50% decrease in intracranial pressures when the animals breathed through an inspiratory impedance of 10 cm H2O using a valve system similar to Example 1.

In all examples above, the intrathoracic pressure decreased relative to the rest of the body, creating a suction effect that reduced the pressure in the venous blood vessels draining the brain, thereby reducing intracranial pressures.

The invention further provides techniques and devices for reducing intracranial pressure (ICP) by facilitating movement of cerebral spinal fluid (CFS). There are a number of causes of increased ICP including: head injury, ischemia, osmolar imbalance, cerebral edema, tumors, complications of dialysis, infections, stroke, hypertensive crises. Each can result in a slow, and in some cases, an acute rise in the ICP. The solid matter of the brain contents makes up about 80–85% of the material enclosed by the skull. Cerebral blood volume accounts for 3–6% and CSF for 5–15%. See, Anesthesia, Third Edition Editor, Ron Miller. Chapter authors: Shapiro and Drummond. Chapter 54 (1990), the complete disclosure of which is herein incorporated by reference. CSF moves within the brain from its site of production to its site of reabsorption in the brain in an unimpeded manner under normal physiological states. Since the contents in the brain are practically incompressible, a change in volume of any one of the three major components (brain matter, blood volume, CSF volume) results in a reciprocal change in one or both of the other brain components. When the volume of the brain expands, secondary to an increase in the non-CSF component(s), some of the CSF is forced to other locations, including through the foramen magnum (hole in skull connecting skull to space where the spinal cord is located) and into the CSF fluid space surrounding the spinal cord. When the non-CSF components expand in volume or size, the intracranial pressure rises. Normal ICP levels are 10–15 mmHg when supine. At levels greater than 15–20 mmHg, damage to the brain can occur secondary to compression and resultant tissue ischemia (lack of adequate blood flow). A reduction in ICP levels can be achieved by a number of clinical interventions including water restriction, diuretics, steroids, hyperventilation, a reduction of cerebral venous pressure, hypothermia, CSF drainage, and surgical decompression.

Increased ICP results in reduced CSF fluid movement and translocation. CSF fluid production generally remains constant (about 150 ml/day) despite elevated ICP. CSF fluid reabsorption is can be slowed by elevated ICP. By using the valve systems described herein, central venous pressures may be reduced. In turn, this results in a decrease in ICP and results in an increase in CSF fluid movement or translocation and reabsorption. This results in a further reduction in ICP.

The valve systems of the invention may be used in spontaneously breathing individuals, in patients ventilated with negative pressure ventilation or in patients ventilated with a ventilator that causes a decrease in central venous pressures for at least a portion of the respiratory cycle. Each time the intrathoracic pressure is reduced with the valve systems of the invention, there is a concomitant reduction in ICP and an increase in the movement of CSF. In other words, there is an increase in the difference between the peak and trough of the ICP wave form when using the valve systems. The sinusoidal movement occurs in spontaneously breathing people because of the change in pressure in the thorax that is transmitted to the brain via the venous blood vessels. The normally fluctuating CSF pressures (the pressure increases and decreases with each inspiration) are altered by the valve systems. More specifically, the valve systems create a lower trough value thereby creating an overall created change in the ICP with each inspiration. In the non-breathing patient, a similar effect can be produced with the valve systems when used with a variety of ventilator devices, including an iron lung, a phrenic nerve stimulator (such as those described in U.S. Pat. Nos. 6,234,985; 6,224,562; and 6,312,399, incorporated herein by reference), a suction cup on the chest that is used to periodically expand the chest and the like.

Figure 9A:
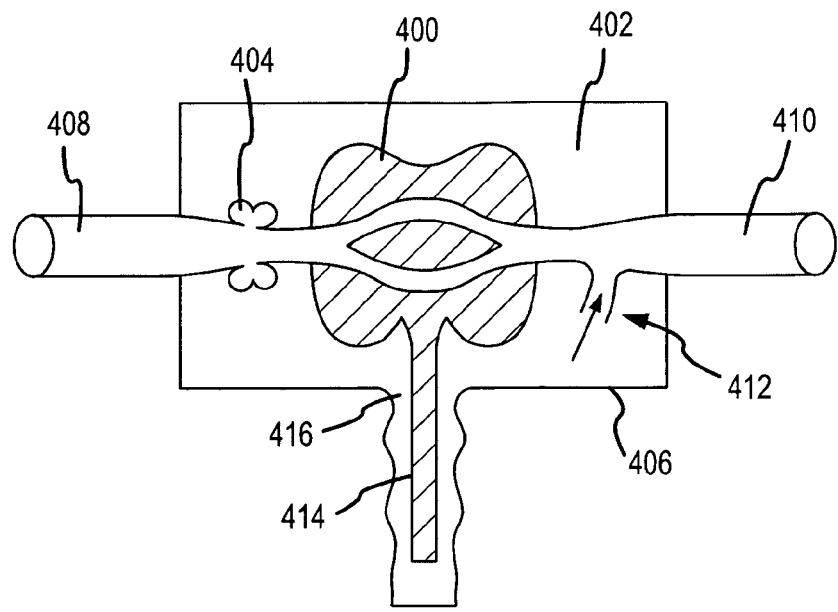
FIG. 9A is a schematic diagram of a person's brain under normal conditions.

Increased CSF fluid movement results in an overall improved metabolic state for the brain. This is shown schematically in FIGS. 9A and 9B. In FIG. 9A, the brain 400 is shown under normal conditions. The brain 400 is surrounded by CSF 402 which is produced at a site 404. The CFS in turn is surrounded by the skull 406. Blood enters brain 400 through an artery 408 and exits through a vein 410. Vein 410 also includes a site 412 of CFS drainage. Shown in FIG. 9A is an arrow showing the direction of CFS flow when draining. Extending from brain 400 is the spinal cord 414 that is surrounded by the foramen magnum 416.

Figure 9B:
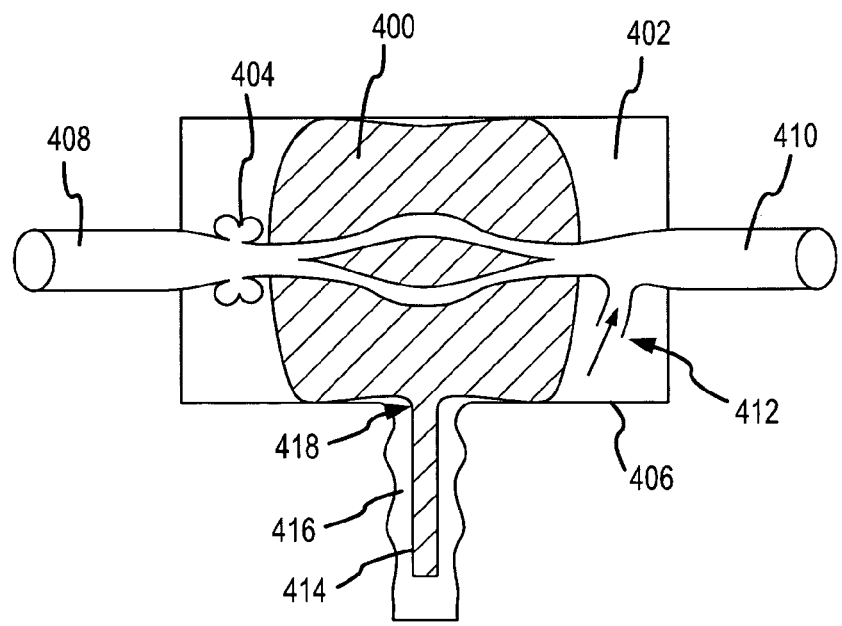
FIG. 9B illustrates the brain of FIG. 9A after increased swelling.

In FIG. 9B, the brain 400 is significantly swollen which reduces the space 402 where the CFS is located. The swelling of the brain 400 can cause blockage of CSF to the spinal cord 414 as shown by arrow 418. Also, movement of CSF to site 412 is reduced to hinder movement of CSF out of the skull 406.

By treating the elevated ICP associated with all of the conditions noted above using the valve systems described herein, brain swelling can be reduced. In so doing, CFS movement and fluid translocation is increased under those same conditions. This results in a further decrease in intracranial pressure as the CSF is able to relocate.

Figure 10:
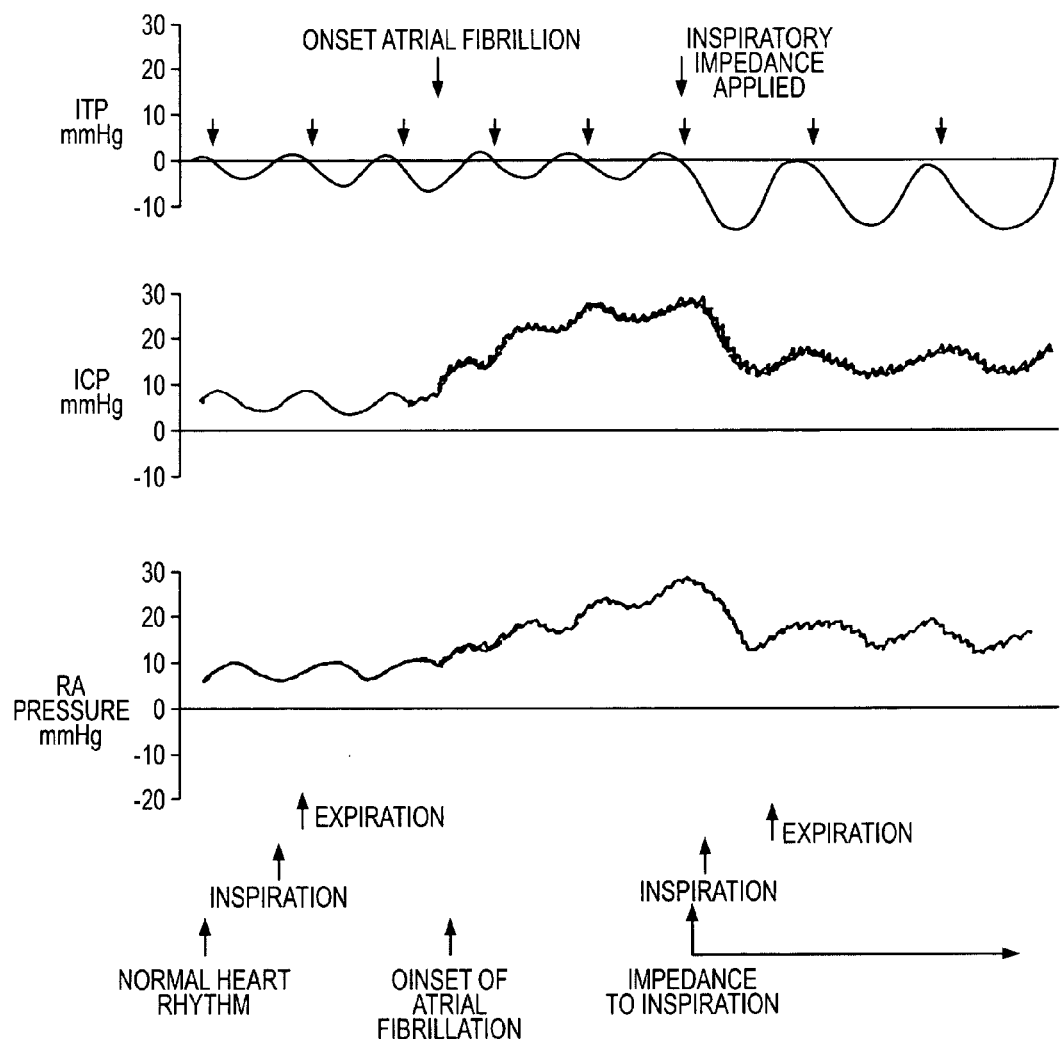
FIG. 10 are three graphs illustrating the effect of lowering intrathoracic pressure on intracranial pressure and right atrial pressure.

Referring now to FIG. 10, the effects of contracting the atria of the heart on ICP will be described. As shown, contraction of the atria results in a phasic movement in ICP. This can be most clearly demonstrated during cardiac ventricular fibrillation. In that setting, the atria often beat spontaneously and the pressure of each contraction and relaxation waveform is transmitted immediately to the brain and is reflected in nearly identical fluctuations in ICP. The inventor has discovered that the fluid systems (venous blood vessels and CSF) are so closely linked, that subtle changes in the heart rhythm result in immediate changes in CSF pressure. Thus, in some patients with significant heart rhythms, or significant heart failure, the rise in right heart pressures as a result of these conditions results in an increase in ICP. Such rises in ICP can lead to a decrease in cerebral perfusion, since cerebral perfusion is determined by the pressure of the blood entering the brain (mean arterial pressure) minus the pressure of the blood leaving the brain (ICP and central venous pressure). Use of the valve and intrathoracic vacuum systems described herein will result in a decrease in intrathoracic pressure. As shown in FIG. 10, the downwardly pointing arrows represent the timing of each inhalation through the valve system. In the baseline state, before the onset of atrial fibrillation, each inspiration (small arrows) results in a reduction in ITP, a reduction of right atria pressure, a reduction in central venous pressures, and then an immediate reduction in ICP. With the onset of atrial fibrillation, the intracranial pressure rises and the sinusoidal pattern of ICP amplitude changes becomes dampened. As soon as the animal begins to inspire through an inspiration impedance of −10 cm H2O there is an immediate decrease in intrathoracic pressure (ITP), an immediate decrease in right atrial (RA) pressures, and an immediate decrease in intracranial pressure (ICP) along with the restoration of a sinusoidal fluctuation in ICP with each inspiration. With elevated ICP, inspiration through the impeding means results in a decrease in ICP, increased cerebral spinal fluid flow, and a decrease in cerebral ischemia secondary to increased cerebral perfusion. As such; the valve systems can used in patients with heart rhythms, such as atrial fibrillation, or patients with heart failure who have increased ICP in order to reduce their ICP, increase CSF fluid movement and translocation, and ultimately help them to improve their brain function.

Hence, the amount of inspiratory resistance, or the amount of negative intrathoracic pressure generation (which may be generated using a variety of techniques) can be controlled or regulated by feedback from measurement of ICP, blood pressure, respiratory rate, or other physiological parameters. Such a system could include a closed loop feedback system.

The invention has now been described in detail for purposes of clarity and understanding. However, it will be appreciated that certain changes and modifications may be practiced within the scope of the appended claims.

What is claimed is:

1. A method for increasing movement of cerebral spinal fluid in a person in need thereof, the method comprising:
coupling a valve system to the person's airway, the valve system being configured to at least periodically prevent respiratory gases from flowing to the person's lungs, wherein respiratory gases are prevented from entering the lungs through the valve system until a negative intrathoracic pressure in the range from about −2 $cmH_2O$ to about −25 $cmH_2O$ is achieved, at which time the valve system permits respiratory gases to flow to the lungs;
repetitively decreasing the person's negative intrathoracic pressure using the valve system when coupled to the person's airway to repetitively lower intrathoracic pressures to thereby increase movement of the cerebral spinal fluid.

2. A method as in claim 1, wherein the person's negative intrathoracic pressure is repetitively decreased by repeatedly inspiring through the valve system.

3. A method as in claim 1, wherein the person's negative intrathoracic pressure is repetitively decreased every other breath, every third breath, or in a repetitive sequence by breathing through the valve system, to reduce intracranial pressure and increase the movement of cerebral spinal fluid.

4. A method as in claim 2, wherein the person spontaneously inspires through the valve system to repetitively decrease the intrathoracic pressure.

5. A method as in claim 2, further comprising artificially causing the person to repeatedly inspire through the valve system.

6. A method as in claim 5, wherein the person is artificially caused to repeatedly inspire by repeatedly stimulating the phrenic nerve, by manipulating the chest with an iron lung cuirass device, by generating negative pressures within the thorax using a ventilator, or by applying a high frequency ventilator that supplies oscillations at a rate of about 200 to about 2000 per minute.

7. A method as in claim 1, further comprising fixing an impedance level of the valve system.

8. A method as in claim 1, further comprising varying an impedance level of the valve system over time.

9. A method as in claim 8, further comprising measuring at least one physiological parameter of the person, and wherein the impedance level is varied based on the measured parameters.

10. A method as in claim 9, wherein the parameters are selected from a group consisting of respiratory rate, intrathoracic pressure, intratracheal pressure, blood pressure, heart rate, end tidal $CO_2$, oxygen level, intracranial blood flows, and intracranial pressure.

11. A method as in claim 1, wherein the valve system is coupled to a mouthpiece, an endotracheal tube, or a face mask that is coupled to the person's airway.

12. The method of claim 1, wherein the person is suffering from head trauma associated with elevated intracranial pressures, and the method treats the person so as to decrease intracranial pressure, at least in part, via increasing movement of cerebral spinal fluid.

* * * * *